United States Patent [19]
Hurd et al.

[11] Patent Number: 5,948,620
[45] Date of Patent: Sep. 7, 1999

[54] REVERSE TWO-HYBRID SYSTEM EMPLOYING POST-TRANSLATION SIGNAL MODULATION

[75] Inventors: Douglas Hurd, Oxford; Rachel Alison Fallon, Littlemore; Nicholas Ian Workman, Aylesbury; Susan Jane Dale, Harrow, all of United Kingdom

[73] Assignee: Amersham International PLC, Buckinghamshire, United Kingdom

[21] Appl. No.: 08/905,377

[22] Filed: Aug. 4, 1997

[30] Foreign Application Priority Data

Aug. 5, 1996 [EP] European Pat. Off. ............. 96112613

[51] Int. Cl.$^6$ ............................ C12Q 1/68; C12N 15/63; C12N 5/10; C12N 15/11
[52] U.S. Cl. ........................ 435/6; 435/7.1; 435/29; 435/69.7; 435/69.8; 435/455; 435/465; 435/483; 536/23.4
[58] Field of Search ................... 435/6, 7.1, 29, 435/69.7, 69.8, 455, 465, 483; 536/23.4

[56] References Cited

U.S. PATENT DOCUMENTS 5,283,173  2/1994  Fields et al. .................. 435/6
5,885,779  3/1999  Sadowski et al. ............ 435/6

FOREIGN PATENT DOCUMENTS

| 0 421 109 A2 | 4/1991 | European Pat. Off. . |
| 195 02 584 A1 | 8/1995 | Germany . |
| 2 276 621 | 10/1994 | United Kingdom . |
| 91/16436 | 10/1991 | WIPO . |

OTHER PUBLICATIONS

E. Baum et al. "β–Galactosidase containing a human immunodeficiency virus protease cleavage site is cleaved and inactivated by human immunodificiency virus protease", Proc. Natl. Acad. Sci., vol. 87, pp. 10023–10027, Dec. 1990.

U. Yavuzer et al., "pWITCH: a versatile two–hybrid assay vector for the production of epitope/activation domain–tagged proteins both in vitro and in yeast", Gene, vol. 165, pp. 93–96, 1995.

*Primary Examiner*—Kenneth R. Horlick
*Attorney, Agent, or Firm*—Wenderoth, Lind & Ponack, L.L.P.

[57] ABSTRACT

The invention relates to modified two-hybrid systems, in particular a reverse two-hybrid system which employs as a reporter a gene encoding a modifying agent such as an enzyme, and a signal agent which is modified by the enzyme usually by being broken down, such that in the event of an inhibition of binding of the two hybrid proteins a detectable signal is produced. The system is particularly useful for drug screening.

9 Claims, 3 Drawing Sheets

1) Reporter

2) Reporter, activator, bait

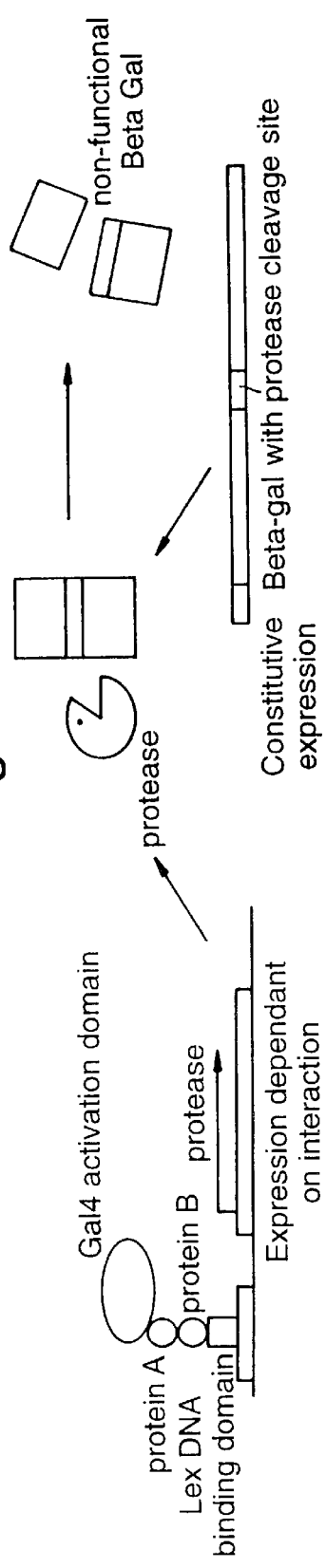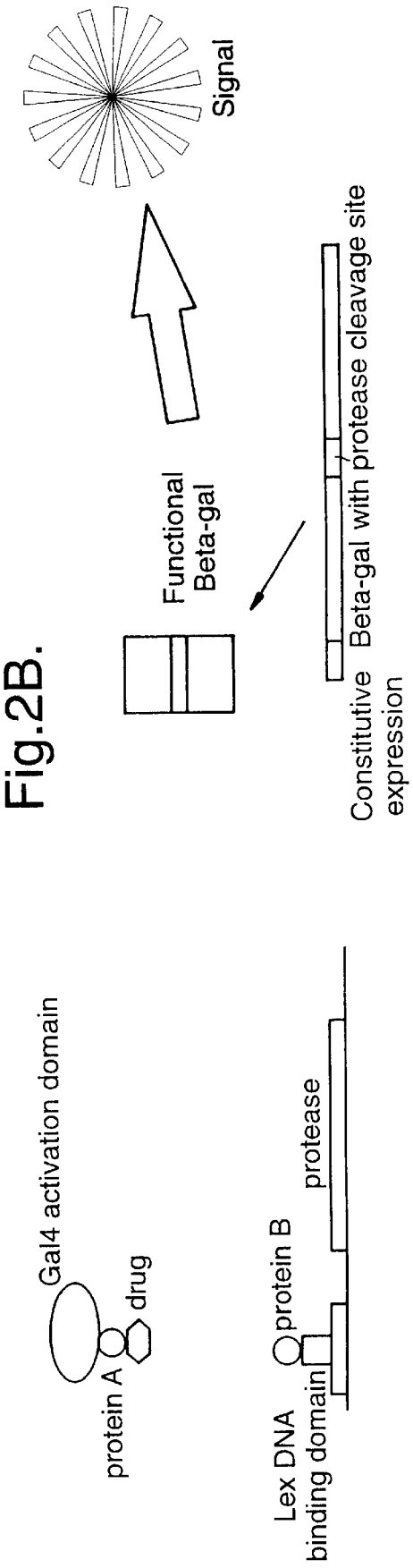

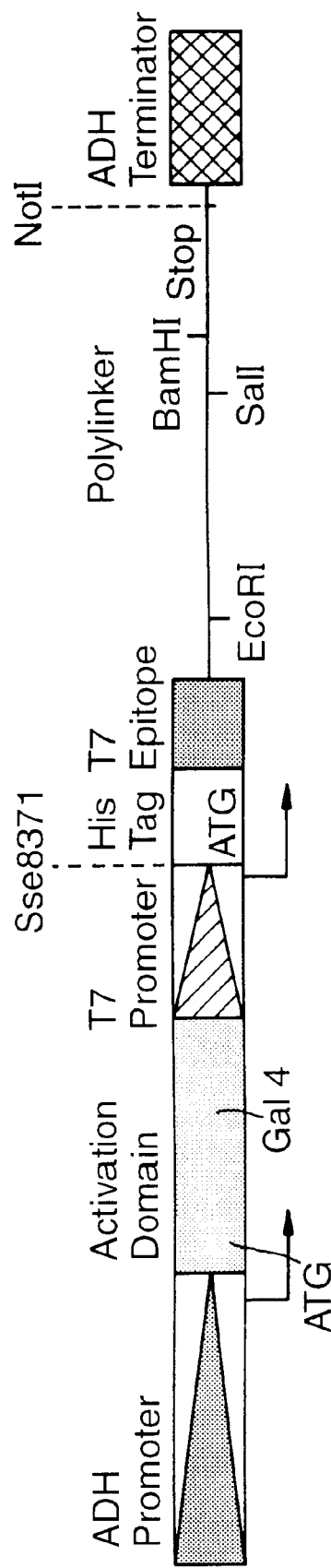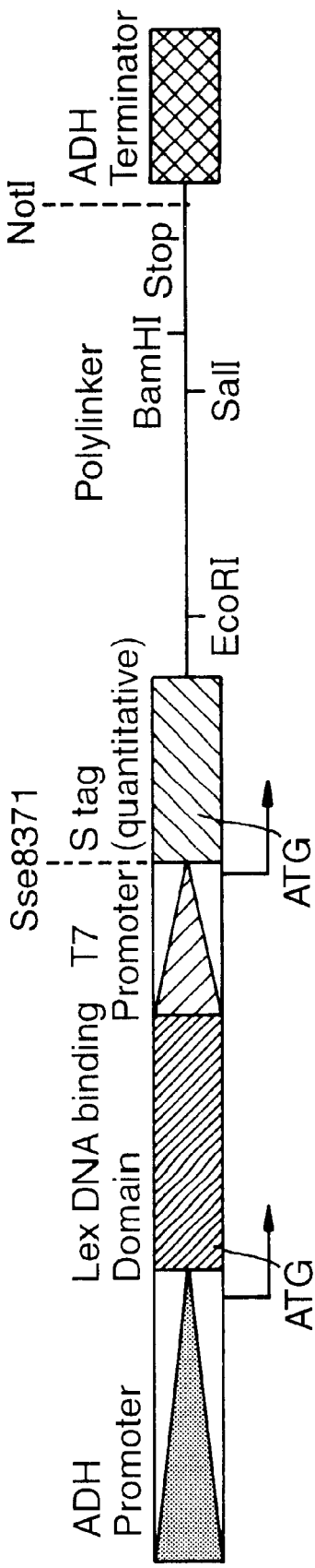

REVERSE TWO-HYBRID SYSTEM EMPLOYING POST-TRANSLATION SIGNAL MODULATION

BACKGROUND OF THE INVENTION

1. Field of the Invention

This invention relates to systems and methods for two-hybrid assays, in particular two-hybrid assays for identifying agents which interfere with protein-protein interactions. The invention further relates to systems and methods for identifying agents which interfere with protein-DNA interactions.

Specific protein-protein interactions are central to biological functions. Protein-protein interactions are intermolecular associations which occur when the surfaces of two or more proteins are precisely matched and a large number of non-covalent bonds form between them. Protein-protein interactions are involved for example in antibody-antigen reactions and in the interaction of cell surface receptors with specific ligands. Clearly the identification of inhibitors of specific protein-protein interactions will be useful for example in developing pharmaceuticals.

2. Description of Related Art

Investigation of protein-protein interactions under physiological conditions has been problematic. One approach has been the so-called "two-hybrid" system of Fields & Song (1) described in U.S. Pat. No. 5,283,173. The two-hybrid system involves the use of two chimeric genes which encode hybrid proteins to test for an interaction between a known protein and protein of interest in vivo. The first chimeric gene codes for a known protein, often called the bait protein, fused to the DNA-binding domain of a transcriptional activator. The second chimeric gene codes for a protein of interest fused to the transcriptional activation domain. Additionally, the protein of interest may not be known and could be derived for example from a cDNA library. In a suitable host cell such as yeast, if the protein of interest and the bait protein do interact they bring into proximity the DNA-binding and transcriptional activation domains. This proximity is sufficient to cause transcription of a marker gene placed under the control of a promoter containing a binding site for the DNA-binding domain.

The two-hybrid system generally allows detection of an interaction between two proteins by means of the positive signal of expression of a reporter gene. In the case of an assay to identify an agent which interferes with a protein-protein interaction, a negative signal indicating inhibition of the interaction might also be produced if the agent being tested is toxic to the cell. Thus, it would be preferable to use a system which gives a positive signal when the protein-protein interaction is inhibited.

WO 95/26400 describes a method for identifying inhibitors of protein-protein interactions using a reverse two-hybrid system, in which the protein-protein interaction drives the expression of a relay gene, which encodes a protein that represses the transcription and thus expression of a reporter gene. This provides indirectly a positive transcriptional read-out for molecules that inhibit the two-hybrid protein-protein interaction.

SUMMARY OF THE INVENTION

In one aspect, the present invention provides a two-hybrid system comprising:
a) a first chimeric gene comprising a DNA sequence which encodes a first hybrid protein, the first hybrid protein comprising a first protein and a DNA-binding domain that recognises a binding site on a reporter gene;
b) a second chimeric gene comprising a DNA sequence which encodes a second hybrid protein, the second hybrid protein comprising a second protein and a transcriptional activation domain;
c) a signal agent which provides a detectable signal; and
d) a reporter gene having a binding site recognised by the DNA-binding domain, which reporter gene encodes a modifying agent which modifies the signal agent so as to alter the detectable signal, the reporter gene being activated to express the modifying agent when the transcriptional activation domain is brought into sufficient proximity to the reporter gene by an interaction between the first and second hybrid proteins.

In another aspect, the invention provides a method of performing a two-hybrid assay, which method comprises:
a) providing a two-hybrid system as described herein;
b) subjecting the host cell to conditions under which the first and second chimeric genes are expressed in sufficient quantity to cause activation of the reporter gene on interaction between the first and second proteins of the two hybrid proteins; and
c) measuring the detectable signal as an indication of whether or to what extent the first and second proteins are interacting.

BRIEF DESCRIPTION OF THE FIGURES

FIG. 2A shows a reverse two-hybrid assay according to the invention in which there is no inhibition of the protein-protein interaction. Protein A and protein B are the two interacting proteins. The DNA-binding domain is shown as a LexA-DNA-binding domain which binds to the LexA operator sequence on the reporter gene. The activation domain is the Gal4 activation domain. The protease enzyme is expressed and cleaves a β-galactosidase signal agent at an engineered cleavage site. The result is that no signal is produced. FIG. 2B shows a drug inhibiting the protein-protein interaction. There is no activation of reporter gene expression by the transcriptional activation domain, there is no protease expression and therefore the β-galactosidase is not cleaved so a positive signal results.

FIGS. 3A and 3B show vectors which may be used in or adapted for use in the invention and which are described in detail in the Examples.

DETAILED DESCRIPTION OF THE PREFERRED EMBODIMENT(S)

Figure 1A:
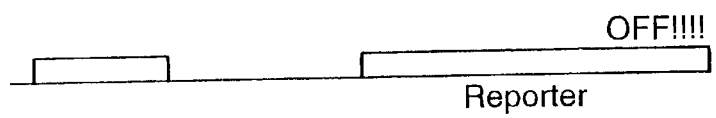
FIG. 1 shows a traditional two-hybrid assay. On protein-protein interaction a signal is produced.
Figure 1B:
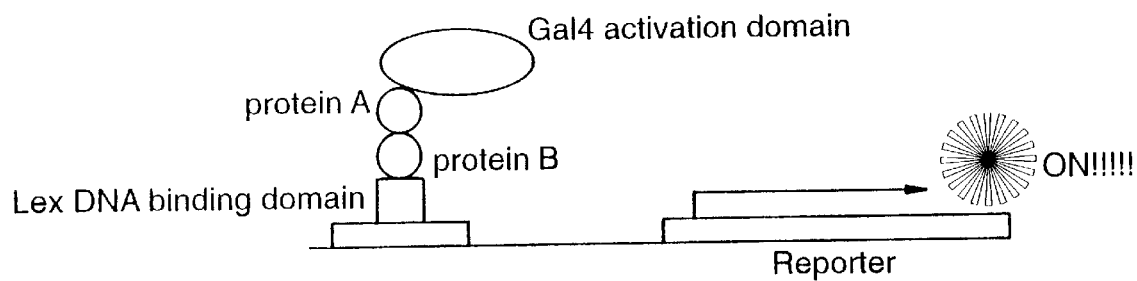

Preferably the first and second proteins of the first and second hybrid proteins are predetermined interacting proteins. Thus the method and system according to the invention will be useful for testing potential inhibitors of the interacting proteins. Generally, in the absence of an inhibitor which interferes with the protein-protein binding, the reporter gene is expressed to produce the modifying agent and the modifying agent breaks down or otherwise modifies the signal agent so that the detectable signal is altered. Generally, the signal agent will be broken down by the modifying agent so that the signal is no longer detectable. However, the signal agent may be modified by the modifying agent so that a different detectable signal is provided. For example, the signal agent may be a photoprotein which is modified by the modifying agent to give a shift in wavelength.

Preferably the modifying agent is an enzyme.

Thus, the invention provides in particular embodiments a reverse two-hybrid system and method, that is a two-hybrid system and method in which a positive signal arises on interference of the interaction between two interacting proteins.

In addition, the invention can be applied to a so-called "one-hybrid" system which may be used in a method for identifying an inhibitor of a specific protein-DNA interaction. DNA-binding proteins bind to specific DNA sequences, for example in the transcriptional regulatory sequences of genes. A one-hybrid system according to the invention comprises the signal agent and reporter gene according to the two-hybrid system, and a single hybrid protein in place of the first and second hybrid proteins. The single hybrid protein comprises a chosen pre-determined DNA-binding domain and a transcriptional activation domain which activates the reporter when in sufficient proximity to it. As with the preferred two-hybrid method and system according to the invention, inhibition of binding in the one-hybrid system results in a positive signal being produced. Further preferred features relating to the reporter gene and signal agent as well as other aspects of the one-hybrid method and system, are as described herein for the two-hybrid method and system.

Preferably the signal agent is a protein encoded by a signal agent gene, which gene is also present in the system and is expressed in the host cell. The signal agent gene is preferably not normally present in the host cell i.e. it is not an endogenous gene in the host cell. Preferably, the enzyme is a protease enzyme which cleaves the protein signal agent so that the signal is no longer detectable. The signal agent gene may have been modified so as to engineer into the signal agent a specific protease cleavage site. For example, the signal agent may be β-galactosidase or luciferase containing a specific protease cleavage site.

The use of a signal agent which is encoded by a signal agent gene and is broken down by e.g. a protease enzyme will provide a rapid switch between positive and negative signals, that is signals indicating inhibition and no inhibition of the protein-protein interaction. A system that uses post-transcriptional modification of the signal agent thus provides advantages over prior art systems. If the protease enzyme is too stable in the host cell for efficient switching to occur, a temperature sensitive protease may be employed together with a suitable temperature regime.

An example of a suitable signal agent for use with the invention is a cleavable β-galactosidase. A cleavable β-galactosidase for use in an assay for protease inhibitors is described in EP 0 421 109 and (2). Another suitable signal agent would be a specially modified bioluminescent protein which may also be cleavable by a protease enzyme. Certain modified bioluminescent proteins are described in WO 91/01305 and (3, 4). A particularly preferred signal agent is one that can be used to provide real-time data, such as luciferase or other photoprotein, or a fluorescent protein.

The reporter gene generally does not behave as a classical reporter gene. That is, in its preferred role expression of the reporter gene leads to the negative signal of the breakdown of the signal agent. However, it will be understood that the reporter gene can also act in the classical way in this invention by leading to a positive signal, if for example the enzyme or other modifying agent encoded by it modifies the signal agent to give a different detectable signal. Thus it is also envisaged that the method and system according to the invention can be used to identify new pairs of interacting proteins.

The reporter gene has, as noted above, a binding site for the DNA-binding domain of the first hybrid protein. The binding site is comprised in a transcriptional regulatory sequence which is positively regulated by the transcriptional activation domain when the activation domain is bound via the interacting proteins to the reporter gene.

Suitable activation domains and DNA-binding domains for use in the invention will be known to those skilled in the art. Examples of DNA-binding domains commonly used in two-hybrid systems are LexA (from E. Coli) and Gal4 (from yeast). The activation domain would be for example the Gal4 activation domain.

Preferably, the host cell is yeast such as Saccharomyces cerevisiae or Schizosaccharomyces pombe. Two-hybrid systems have been most widely studied in yeast. However, other eukaryotic cells such as mammalian cells or cells from Drosophila or baculovirus are not excluded. A mammalian two-hybrid drug assay system is considered possible and may be preferable as it would represent more closely the physiological conditions under which a potential drug candidate would be required to work.

The reporter gene, the signal agent gene and the chimeric genes encoding the two hybrid proteins may all be maintained episomally. Thus, they may be present on one or more expression vectors such as plasmids. Preferably some, or more preferably all of the genes are integrated into the host cell genome. Stable integration into the genome means that it is not necessary to continually select for host cells containing all the elements required for the two-hybrid system. Integration sites in the genome need to be chosen to ensure adequate expression levels of the various genes (5, 6). The required level of expression of each gene will depend upon factors such as the level of interaction of the interacting proteins, and on the potential toxicity of the hybrid proteins.

A test inhibitor in the method or system according to the invention may be a chemical or a biochemical agent introduced from outside the host cell. In that case, the host cell may need to be suitably permeable to allow entry of the agent into the cell. Alternatively, the test inhibitor may be encoded by a polynucleotide and be introduced into the cell by providing the polynucleotide sequence encoding it and causing the test inhibitor to be expressed in the host cell. This will be very useful in the cloning of genes whose gene products interfere with a specific protein-protein interaction. Using the method or system according to the invention a peptide, genomic or cDNA library can be screened for genes or polynucleotide sequences whose expression products interfere with a particular protein-protein interaction.

As already mentioned, where a potential inhibitor is introduced from outside the cell, the cell will need to be permeable enough to allow it to enter. Also, if any substrate or co-factor is required for the enzyme to act on the signal agent, it must also be possible for the substrate or co-factor to enter the cell. The yeast cell wall is permeable to most molecules under 1000D. There are methods known in the art for increasing permeability of the yeast cell wall, or cell wall mutants may be used. Other possibilities are to use sphaeroplasts or to treat cells with compounds such as polymyxin B. Depending on the particular host cell used and on the nature of the test inhibitor and any substrate or co-factor, it may or may not be necessary to take extra steps to ensure sufficient permeability of the host cell.

The invention is not limited in the type of transcription system it may be used with. Thus, transcription systems based on RNA polymerase I, II and III are all included.

The pair of interacting proteins may be from any source. They are "pre-determined" interacting proteins in that they are known to be capable of interacting with one another by specific binding. The pair of interacting proteins may be chosen according to the particular studies being undertaken. These may be fundamental studies relating to e.g. identification of cell signal transduction pathways or they may be commercially directed such as for identification of new drugs or genes useful in gene therapy. It will be evident that the word "protein" as used here in the context of interacting proteins and signal agents covers peptides, polypeptides and related molecules.

The interaction between the pair of pre-determined interacting proteins may depend upon one (or both) of the proteins being modified in a specific way. For example, the interaction may only take place if one of the proteins is phosphorylated. An appropriate kinase will then be needed and may be provided by including in the system a gene encoding the kinase. Such a system may be referred to as a "tri-hybrid" system, (7).

The system according to the invention for e.g. identifying inhibitors may be provided in the form of a kit. A suitable format for such a kit would be for example a microtitre plate of the standard 96-well type, some or all of the wells containing yeast or other eukaryotic host cells according to the invention.

It will be evident that the use of suitable controls with the method according to the invention may be appropriate or necessary. For example, in a test for an inhibitor of a protein-protein interaction, a drug that inhibits the enzyme encoded by the reporter gene will be identified as positive. Either a control or a secondary screen may be desirable in order to eliminate such false positives.

REFERENCES
1. Fields, S. and Song, A. -K. (1989) Nature 340: 245–246.
2. Baum, E. Z., Bebernitz, G. A. and Gluzman, Y. (1990) PNAS 87: 10023–10027.
3. Waud, J. P. et al (1996) Biochim Biophys Acta 1292: 89–98.
4. Sala-Newby, G. and Campbell, A. K. (1992) FEBS Lett 307: 241–4.
5. Feilotter, H. E. et al, NAR 22 (8): 1502–1503.
6. Bartel, P. (1993) In Hartley, D. A. (ed.) "Cellular Interactions in Development: A Practical Approach", Oxford University Press, Oxford, 153–179.
7. Osbourne, M. A., Dalton, S. and Kochan, J. P. (1995) Biotechnol. 13: 1474–1478.

EXAMPLES

An aim of the present invention is to provide a strategy for screening a bank of agents with a reverse 2-hybrid system to identify agents that inhibit the intermolecular association of two interacting polypeptide sequences. The assay comprises a signal agent which can be expressed constitutively, a DNA binding domain fusion construct or "bait vector" containing one of a pair of interacting polypeptide sequences, a reporter gene having a binding site recognised by the DNA binding domain and a transcriptional activator fusion construct containing the second of a pair of interacting polypeptide sequences and a suitable yeast strain. All vectors may be maintained episomally in the host organism for the assay or alternatively integrated into the host's genome.

The following examples illustrate the invention

Generally, the nomenclature used hereafter and the laboratory procedures in cell culture, molecular genetics and nucleic acid chemistry described below are those well known and commonly employed in the art. Standard techniques are used for recombinant nucleic acid methods, polypeptide synthesis, microbial culture and transformation. Generally, enzymatic reactions and purification steps are performed according to manufacturer's instructions. The techniques and procedures are generally performed according to conventional methods in the art and various general references such as Sambrook et al, 1989 and Guthrie et al (1991)

1. Construction of reagents for the assay (a) Construction of the reporter gene vector The plasmid pSD1 contains the GAL1-10 basal promoter (bp 488–822, EMBL accession number k02115), with an XhoI site upstream and a EcoRI site at the 3' terminus. Downstream of the EcoRI site is the CYC1 transcriptional terminator sequence. The plasmid contains a TRP1 marker. The coding region for the HIV-1 protease (BBG 40, R&D Systems, Abingdon, UK), is inserted in frame into the EcoRI site. The reporter gene must be operably linked to a promoter which is responsive to a DNA binding domain such as LexA. An oligonucleotide encoding a LexA operator sequence (WO 94/10300) is inserted into the XhoI site. Therefore binding of a LexA DNA binding domain complex containing a transcriptional activation domain will result in the expression of the HIV-1 protease.

One possible drawback of the system is the half life of the protease, which results in the need for incubation with the inhibitor for long periods of time. In order to overcome this possible limitation, the protease sequence is modified further such that a temperature sensitive protease is expressed. An example of a temperature sensitive HIV-1 protease mutant is LysPR3-25 (Rockenbach et al, 1990), which has the extra residiues Met-Lys-Asn-Phe at the N-terminus of the protease. By incubating the yeast culture at higher temperature (42° C.) prior to adding the inhibitor (at 30° C.), most of the pre-existing intracellular protease will be inactivated before addition of the inhibitor and the kinetics of the assay is therefore improved.

Other strategies to improve the kinetics of the assay are to manipulate the HIV-1 protease to include PEST sequences (Rogers et al), KFERQ motifs (Dice et al) or cyclin destruction boxes (Glotzer et al, 1991). Other modifications of the HIV protease are constructed based on these approaches and tested for improved kinetics in the assay described in 2. below.

(b) Construction of the vector encoding the signal generating agent

A plasmid derived from pLGΔ312S (Guarente and Mason, 1983) with a LYS2 selectable marker. The LacZ is expressed constitutively from a CYC1 promoter. The LacZ has been modified according to Baum et al, 1990, with an HIV-1 protease cleavage site (coding for Val-Ser-Phe-Asn-Phe-Pro-Gln-Ile-Thr-Leu) inserted at the Sau3A site at nucleotide 239 of LacZ.

(c) Construction of the activator vector pDM22 is an activator plasmid shown in FIG. 3A (and described in WO 96/30507) encoding the GAL4 transcriptional activation domain expressed from a yeast ADH1 promoter. Downstream of the transcriptional activation domain is a translationally in frame T7 promoter which is functional in vitro and in certain strains of E. coli (e.g. BL21: Novagen). Downstream of the T7 promoter are two tags, a (histidine)$_6$ tag for purification of proteins (Hochuli et al, 1988) and a T7 epitope tag (Lutz-Freyermuth et al, 1990). Following the tags is a polylinker for cloning the gene of interest and translation stop codons, followed finally by the ADH1 terminator. The plasmid pDM52 is similar to pDM22; however, in pDM52 the ADH1 promoter is replaced by the MET25 promoter (Mumberg et al). Downstream of this promoter is the GAL4 activation domain, the T7 promoter, a polylinker and the ADH1 terminator. In between the ADH1 and the GAL4 activation domain is a unique SpeI site. At the 3' termini of the GAL4 activation domain is a BgIII site. All constructions are carried out using standard techniques.

(d) Construction of the bait plasmid

The plasmid pDM26 shown in FIG. 3B contains the ADH1 promoter which expresses the LexA DNA binding domain, a translationally in frame T7 promoter, an S tag, a polylinker, translation stop codons and finally an ADH1 terminator. Downstream of the LexA DNA binding domain is a polylinker into which a suitable gene encoding a polypeptide of interest can be cloned. Following the polylinker is an ADH1 terminator. The construction of this plasmid is carried out using standard molecular techniques.

All constructs are integrated into the yeast if required by standard techniques (Guthrie et al, 1991).

2. Demonstration of the assay in the presence of a protein interaction

It has been shown that truncated ATF2 and cJun proteins interact (Du et al, 1993). The cJun fragment is introduced in frame by standard cloning techniques into the polylinker of the "activator vector" described above. The ATF2 gene is introduced in frame into the polylinker of the bait plasmid (described above) also by standard cloning techniques. The cJun activator and ATF2 bait plasmids are both transformed by standard techniques into a yeast strain (*S. cerevisiae:* YM4136 (Feilotter et al, 1994 (5)), which has the genotype MATα ura3-52 his3-200 ade2-101 lys2-801 trp1-901 leu2-3, 112 gal80-538) containing the reporter gene and the signal generating agent, both described in 1 above (test cells). The yeast cells are assayed for β-galactosidase activity as described previously (Harshman et al, 1988) and the signal compared with that from yeast containing either the ATF2 bait plasmid, the reporter and the signal generating agent or the cJun activator plasmid, the reporter and the signal generating agent or the signal generating agent and reporter alone or the signal generating agent alone or the reporter alone (control cells). A series of measurements are taken over time. All variations of the signal generating agent described in 1(a) are compared in this assay and the kinetics of the each assay relative shown relative to the other.

3. A Western blot to show expression of the signal agent with time in the presence of a protein interaction Test and control yeast cells together with wild type yeast were prepared as described in 2 above the yeast cultures were sampled at different times, lysed using standard techniques and subjected to SDS-PAGE followed by Western blotting. The membrane is probed with an antibody to HIV protease according to standard techniques and detected using ECL reagents (Amersham International plc).

4. Demonstration of the reverse 2-hybrid assay in the presence of a small molecule which inhibits a model protein:protein interaction The screening method described in this invention can be used to screen for a small molecule that will inhibit an interaction between two polypeptides of choice. In order to demonstrate the principle of such a screen, the disruption of the interaction between the hormone binding domain of the oestrogen receptor and the heat shock protein HSP90 by oestradiol is shown. This model system is described in U.S. Pat. No. 5,525,490. The hormone binding domain of the oestrogen receptor is cloned into the "activator vector" and the heat shock protein HSP90 is cloned into the bait vector. (Both polypeptide sequences are generated from human genomic DNA by PCR and cloned into the vectors described by standard techniques). The vectors are introduced into yeast and assayed for β-galactosidase activity as described in 3. above. Inhibition of the protein interaction by estradiol is indicated by increased expression of β-galactosidase compared with the control cells not treated with oestradiol.

5. Demonstration of the reverse 2-hybrid assay in the presence of a polypeptide which inhibits a model protein-:protein interaction Potentially inhibitory polypeptide sequences are introduced into the test and control yeast cells described in 5. above using standard transformation techniques and under conditions wherein the polypeptide is expressed ex vivo. The polypeptides are in the form of either a genomic DNA, a cDNA or a peptide expression library. The cells are assayed for β-galactosidase activity as described. Plasmids encoding inhibitory polypeptides discovered in the screening method of this invention can be recovered from the library as described in U.S. Pat. No. 5,525,490.

REFERENCES

Baum, E., Z., Bebernitz, G. A. and Gluzman, Y. (1990) PNAS 87 10023–10027.

Dice, J. F. (1990) Trends Biochem. Sci. 15 305–9.

Du, W., Thuros, D. and Maniatis, T. (1993) Cell 74 887–898

Feilotter, H., Hannon, G. J., Ruddell, C. J. and Beach, D. (1994) Nucl. Acids Res. 22 1502–1503.

Glotzer, M.; Murray, A. W. and Kirschner, M. W. (1991) Nature 349 132–138

Guarente, L and Mason, T. (1983) Cell 32 1279–86.

Guthrie, C. and Fink, G. R. (1991) Methods in Enzymology 194

Harshman, K. D. et al. (1988) Cell 53 321–330

Hochuli, E., Bannwarth, W., Dobeli, H., Gentz, R. and Stuber, D. (1988) Biotechnology 6 1321–1325

Jayaraman, P. S., Hirst, K. and Goding, C. R. (1994) EMBO J. 13 2192–2199

Lutz-freyermuth, C., Query C. C. and Keene, J. D. (1990) Proc. Natl. Acad. Sci. USA 87 6393–6397

Mumberg, D., Muller, R. and Funk, M. (1994) Nucl. Acids Res. 22 5767–8

Rockenbach, S. K., Olsen, M. K. and Tomich, C -S. C. (1990) AIDS Res and human retroviruses 6 543–552.

Rogers, S., Wells, R. and Rechsteiner, M. (1986) Science 234 243–368

Sambrook, J., Fritsch, E. F. and Maniatis, T. Molecular Cloning: A laboratory manual, 2nd Edition (1989) Cold Spring Harbor Laboratory press, Cold Spring Harbor, N.Y.

We claim:

1. A two-hybrid system comprising:
   a) a first chimeric gene comprising a DNA sequence which encodes a first hybrid protein, the first hybrid protein comprising a first protein and a DNA-binding domain that recognizes a binding site on a reporter gene;
   b) a second chimeric gene comprising a DNA sequence which encodes a second hybrid protein, the second hybrid protein comprising a second protein and a transcriptional activation domain;
   c) a signal agent gene encoding a signal agent which provides a detectable signal, the signal agent gene being activated to express the signal agent independently of any interaction between the first and second hybrid proteins; and
   d) a reporter gene having a binding site recognised by the DNA-binding domain, which reporter gene encodes a modifying agent which is an enzyme which modifies the signal agent so as to alter the detectable signal, the reporter gene being activated to express the enzyme when the transcriptional activation domain is brought into sufficient proximity to the reporter gene by an interaction between the first and second hybrid proteins.

2. The system as claimed in claim 1, wherein the first and second proteins of the first and second hybrid proteins are predetermined interacting proteins.

3. The system as claimed in claim 1, wherein the modifying agent is an enzyme which modifies the signal agent so that the signal is no longer detectable.

4. The system as claimed in claim 3, wherein the enzyme is a protease which specifically breaks down a protein signal agent.

5. The system as claimed in claim 1, in a eukaryotic host cell.

6. A method of performing a two-hybrid assay, which method comprises:
   a) providing a system as claimed in claim 5;
   b) subjecting the host cell to conditions under which the first and second chimeric genes are expressed in sufficient quantity to cause activation of the reporter gene on interaction between the first and second proteins of the two hybrid proteins; and
   c) measuring the detectable signal as an indication of whether or to what extent the first and second proteins are interacting.

7. The method as claimed in claim 6, for detecting an inhibition of an interaction between a pair of interacting proteins, wherein the first and second proteins of the two hybrid proteins are predetermined interacting proteins, the method further comprising introducing a test inhibitor into the host cell and measuring the detectable signal to determine whether the unmodified signal agent is present to a greater degree in the presence of the test inhibitor compared to in the absence of the test inhibitor and thus to determine whether the test inhibitor inhibits the interaction between the two interacting proteins.

8. The method as claimed in claim 7, wherein the test inhibitor is a chemical or biochemical agent introduced from outside the host cell.

9. The method as claimed in claim 7, wherein the test inhibitor is encoded by a polynucleotide which is introduced into and expressed in the host cell.

* * * * *